US010234363B2

(12) United States Patent
Curtis

(10) Patent No.: US 10,234,363 B2
(45) Date of Patent: Mar. 19, 2019

(54) AUTOMATIC LIQUID WASTE RESERVOIR LEVEL CONTROL

(71) Applicant: Mustang Sampling LLC, Ravenswood, WV (US)

(72) Inventor: Micah A. Curtis, Ravenswood, WV (US)

(73) Assignee: Mustang Sampling LLC, Ravenswood, WV (US)

( * ) Notice: Subject to any disclaimer, the term of this patent is extended or adjusted under 35 U.S.C. 154(b) by 0 days.

(21) Appl. No.: 15/862,170

(22) Filed: Jan. 4, 2018

(65) Prior Publication Data

US 2018/0209875 A1 Jul. 26, 2018

Related U.S. Application Data

(60) Provisional application No. 62/449,346, filed on Jan. 23, 2017.

(51) Int. Cl.
| | | |
|---|---|---|
| *F17C 5/00* | (2006.01) | |
| *G01N 1/22* | (2006.01) | |
| *G01N 1/18* | (2006.01) | |
| *G01N 33/22* | (2006.01) | |
| *G01N 33/00* | (2006.01) | |
| *G05D 9/00* | (2006.01) | |
| *G01N 1/40* | (2006.01) | |

(52) U.S. Cl.
CPC ........... *G01N 1/2247* (2013.01); *F17C 5/002* (2013.01); *G01N 1/18* (2013.01); *G01N 33/0016* (2013.01); *G01N 33/225* (2013.01); *G05D 9/00* (2013.01); *F17C 2221/033* (2013.01); *F17C 2225/033* (2013.01); *G01N 2001/4033* (2013.01)

(58) Field of Classification Search
CPC .. B67D 7/04; B67D 7/72; E03C 1/122; F16K 11/056; F17D 1/12; G05D 7/01; G05D 9/00; G05D 9/02; G05D 7/0166; F17C 2221/033; F17C 2225/033; F17C 5/002; G01N 1/18; G01N 1/2247; G01N 2001/4033; G01N 33/0016; G01N 33/225; Y10T 137/7303
USPC ....................................................... 137/391
See application file for complete search history.

(56) References Cited

U.S. PATENT DOCUMENTS

| | | | |
|---|---|---|---|
| 3,530,990 A | 9/1970 | Grimshaw | |
| 3,645,398 A * | 2/1972 | Fiocco | B01D 17/0211 516/137 |
| 4,412,924 A * | 11/1983 | Feather | C02F 1/78 210/123 |
| 4,696,718 A * | 9/1987 | Lasater | B01D 1/02 202/176 |
| 4,948,010 A | 8/1990 | Wiggins | |
| 5,005,615 A | 4/1991 | McGarvey et al. | |
| 5,090,242 A | 2/1992 | Hilton | |
| 5,287,886 A | 2/1994 | Russell | |

(Continued)

OTHER PUBLICATIONS

International Search Report and Written Opinion of PCT/US2018/014141, dated May 15, 2018.

*Primary Examiner* — William M McCalister
(74) *Attorney, Agent, or Firm* — Cahn & Samuels, LLP

(57) ABSTRACT

Systems and methods for automatically purging by pneumatic ejection with a select pressurized media, gravity-accumulated hydrocarbon liquid dropout from a retrograde vapor waste liquid collection containment reservoir.

9 Claims, 2 Drawing Sheets

(56) References Cited

U.S. PATENT DOCUMENTS

| | | | | |
|---|---|---|---|---|
| 5,538,598 A | * | 7/1996 | Schlesinger | B01D 1/0017 |
| | | | | 202/197 |
| 5,616,217 A | * | 4/1997 | Taylor | B01D 3/40 |
| | | | | 203/3 |
| 6,197,162 B1 | * | 3/2001 | Quiros | B01D 3/10 |
| | | | | 159/16.1 |
| 6,299,781 B1 | * | 10/2001 | Hanrahan | B01D 19/0052 |
| | | | | 205/338 |
| 6,695,017 B1 | | 2/2004 | Liedtke | |
| 6,761,195 B2 | * | 7/2004 | Airaksinen | F16N 19/006 |
| | | | | 141/198 |
| 7,087,157 B2 | | 8/2006 | Spani | |
| 8,343,316 B2 | * | 1/2013 | Williams | B01D 1/14 |
| | | | | 159/16.1 |
| 8,501,019 B2 | * | 8/2013 | Schomburg | B01D 1/20 |
| | | | | 210/188 |
| 8,973,437 B2 | | 3/2015 | Cantolino | |
| 2002/0133869 A1 | | 9/2002 | Pondelick et al. | |
| 2010/0213083 A1 | | 8/2010 | Olande et al. | |

* cited by examiner

AUTOMATIC LIQUID WASTE RESERVOIR LEVEL CONTROL

PRIORITY CLAIM

This application claims priority of U.S. Provisional Application Ser. No. 62/449,346 filed Jan. 23, 2017.

FIELD OF INVENTION

This invention relates to an automatic detection system and method for purging gravity-accumulated hydrocarbon liquid dropout from a retrograde vapor waste liquid collection containment reservoir.

BACKGROUND

The automation of industries that rely on multi-step processing systems had led to increased efficiency, reduced economic loss, greater value returns on raw resources, as well as improved time efficiency and system accuracy. The natural gas processing and sampling industry benefits from automation in the same way. Many aspects of the gas processing and sampling industry are currently automated.

Though many aspects of the process are automated, automation is currently absent specifically in the level detection and purging of condensate by-product containment reservoirs of gas sampling and conditioning systems. The current technological state in the context of energy fuels and particularly, natural gas production, results in decreased system efficiency. Specifically, unautomated waste containment reservoirs that receive the condensate dropout from gas conditioning lines increase costs and contribute to adverse environmental impact, resource use efficiency, labor, and regulatory compliance.

In the context of systems used for gas sampling, conditioning, and analysis, a sample is conditioned at designated temperature, pressure, and flow rate to be passed through the analyzer. For example, gas chromatography is a conventional method for sample analysis in such systems. In the gas analysis step, a small proportion of the total conditioned stream is used for analysis. The remainder of the gas stream passes through the analyzer and requires downstream disposal. The vaporized content of the gas line typically condenses downstream of the analyzer due to temperature and pressure reductions where the liquid dropout may be collected in a reservoir. In the case that the collection vessel or reservoir fills beyond capacity, a backup results that may damage the analyzer. Therefore, a need exists to minimize the risk of condensate back up into the reservoir vent header.

In the absence of waste containment automation, the drainage of condensate containment reservoirs in particular can result in environmentally harmful methods of waste disposal such as flaring or venting, draining and dumping. As the markets for cleaner energy from natural gas output grow, the effects of fugitive gas released throughout the natural gas production process is of increasing concern.

Release of potentially harmful wastes during, for example, the processing of natural gas conditioning, contributes to the problems relating to pollution that result from unmediated disposal practices. For example, gas flaring generates heat and noise that can be disruptive to the surrounding environment and unnecessarily consumes products that have the potential for reintroduction in the processing system or disposal of in a more environmentally sound manner. Gas flaring also often requires a pilot light type flame to be constantly burning, exposing the system to unnecessary susceptibility to the risk of unexpected combustion.

Detrimental impacts result from immediate release by dumping or draining of liquid dropout by-products directly to the ground and the surrounding environment. However, the participant risks potential liability, both civil and criminal, based on the particular circumstances. Automation of condensate containment reservoir drainage will decrease a system's dependence on inefficient and potentially unlawful methods of disposal by directing the system to controllably release a predesignated amount of condensate to a designated source under pre-specified conditions.

Additionally, byproducts of natural gas processing may have intrinsic value, particularly in view of the progress in reclamation technology. Therefore, unrestricted disposal may, in fact, lead to avoidable economic loss. Economic value can be derived by collecting such liquid dropout byproduct materials previously regarded as waste, for reclamation, recycling, or further processing, thus making the cost of inefficient draining and lost resources even greater. The industry will benefit from the development of an automatic control that allows a processing system to more consistently, precisely, and accurately measure and direct the liquid condensate byproduct that is formed as a result of natural gas processing.

Efficiency is decreased when a system has to rely on manual labor for completion of certain tasks. An example of manual intervention currently implemented in this field is where a reservoir tank features a sight glass allowing a maintenance engineer to view the contents of the tank, informing him or her to make a determination whether to initiate the containment reservoir purging process. Requiring manual observation of the levels of condensate inside a containment reservoir and manual intervention to cause purging of the reservoir system results in unnecessary costs to the industry, while also introducing a greater probability for user error or undesirable outcomes. Automation of the system tank purging will also reduce the probability of undesirable overfilling, flooding, and liquid back-up from the reservoir that can result from inattentive visual observation. The automation of the containment reservoir level control step additionally would allow the system to maintain accurate record-keeping of the rate of flow and volume of condensate output of a reservoir tank via maintenance of a record of the level sensor signal events.

Therefore, a need exists for improvement to the presently accepted and commonly used systems and methods of detection of waste containment reservoir levels to ensure that disposal is done in more efficient and practicable ways. Specifically, a need exists for an automatic control for reservoir container waste levels.

SUMMARY OF THE INVENTION

It is an object of the present invention to overcome shortcomings present in the existing state of the art.

It is an object of the present invention to provide a solution to the economic and environmental burden created by ineffective control of engagement containment reservoirs from improper disposal and/or purging, particularly in cases of volatile carbon by-products produced in the processing of natural gas.

It is another object of the invention to reduce the risk of analyzer damage as a result of sample condensate dropout backing up from the containment reservoir into a vent header and to the analyzer.

It is another object of the invention to provide a containment reservoir level control that reduces error.

It is another object of the invention to provide a containment reservoir level control that can automatically detect the volume of condensates accumulated in a reservoir and periodically cause the removal of the accumulated condensation in a controlled manner without system shutdown.

These and other objects are satisfied by a system for liquid waste reservoir level control comprising: a vent header in fluid communication with a source of liquid dropout condensate, a containment reservoir including containment reservoir input and a containment reservoir output, said containment reservoir output being in fluid communication with a liquid drain line, a multi-directional valve incorporating at least a first, second, and third communicating orifices, said vent header being in fluid communication with and connected to said first communicating orifice, said third valve orifice being in fluid communication with said containment reservoir input, a pneumatic pressure source, said pneumatic pressure source being in communication with said containment reservoir, a sensor disposed in the containment reservoir, said sensor being programmed to detect a containment reservoir liquid level, and an electrically energizable solenoid valve disposed between said pneumatic pressure source and said containment reservoir, said actuatable solenoid valve being in signal communication with said sensor.

These and other objects are satisfied by a method of controlling containment reservoir liquid level with a system including a multi-directional valve, an electrically energizable solenoid valve, a source of pneumatic pressure, and a liquid level sensor, the method comprising the steps of: sensing the liquid level from the liquid containment reservoir, communicating via signal communication when the liquid level is detected to exceed a pre-set maximum, energizing the electrically energizable solenoid valve upon detection of the signal from the liquid level sensor, closing the multi-directional valve to inhibit further accumulation of liquid in the liquid containment reservoir, opening the multi-directional valve to enable pressurizable communication between the pressure source and the liquid containment reservoir, and releasing pressurized media from the pressure source.

The invention herein is useful for minimizing undesirable overfilling and liquid back-up from the reservoir while facilitating environmental compliance by reducing the need for flaring or draining dropout liquid directly into the ground while promoting reclamation, recycling and/or use of the dropout fluid in a controlled manner. The invention provides for controlled reservoir purging and liquid disposal. In a fully automated form, the invention also reduces labor and operator exposure by avoiding the need to continuously monitor collected liquid levels, and the need to periodically shut down the dropout collection system for manual discharge/disposal of the collected fluids in the reservoir. Because natural gas liquid ("NGL") and other hydrocarbon liquids are also susceptible to phase transition vaporization, the risk of generating an unsafe vapor pressure within the tank is also minimized. The invention provides for removal of condensates in a liquid waste dropout tank when the detected condensate level exceeds a predetermined maximum. Depending on the specific application and facility, the system herein can be implemented for use in relatively larger scale, e.g. 50-gallon reservoirs or much smaller collection vessels, e.g., 1-liter reservoirs.

This invention is particularly complementary to gas sampling, conditioning, and analyzing systems that generate liquid condensates during processing to drain the liquid condensates to a collecting reservoir. Exemplary conditioning systems include, for example, low-pressure NGL vaporization and measurement systems, low-pressure biogas sample takeoff and conditioning systems, and composite gas sampling systems, such as those described and disclosed respectively in U.S. Pat. No. 9,057,668; U.S. Pat. No. 9,535,045; and U.S. Pat. No. 9,562,833; the contents of which are incorporated by reference herein.

More particularly, the invention is directed to systems and methods for controlled recovery of natural gas processing dropout condensates, e.g., NGLs, generated during sample analysis processing that are drained by gravity via a vent header, as for example, an analyzer or conditioning instrumentation housing to a containment reservoir input. In a described embodiment, the system incorporates a multi-directional valve switch proximate to the containment reservoir input port which itself is controlled by an actuator that preferably is a remotely-spaced, actuatable solenoid valve that actuates upon receiving a signal corresponding to a maximum permissible fluid level from a float switch disposed in the containment reservoir to stop additional discharge into the reservoir while coincidentally directing pressurized air/gas to pressurize the reservoir and discharge the liquid through an outlet line proximate to the bottom of the reservoir. An outlet line directs the pressurized fluid to a select destination which can be any of, for example, reinjection into the original process stream, input to a reclamation tank for additional treatment/extraction/processing of beneficial content, passing to a heat/electricity co-generating facility, etc.

The invention also facilitates environmental regulatory compliance by directing controlled reservoir purging to a predetermined controlled end location in lieu of flaring and/or other disposal methods. Most particularly, the invention provides a system and method for controlling the flow to and from a gravity-fed waste dropout collecting reservoir. Further objects and advantages of this invention will become apparent from a consideration of the drawings and ensuing descriptions.

Particular terminology used herein is for the purpose of describing particular embodiments only and is not intended to be limiting of the invention.

As used herein, the singular forms "a," "an," and "the" are intended to include the plural forms as well, unless the context clearly indicates otherwise. It will be further understood that the root terms "include" and/or "have," when used in this specification, specify the presence of stated features, steps, operations, elements, and/or components, but do not preclude the presence or addition of at least one other feature, step, operation, element, component, and/or groups thereof.

As used herein, the terms "comprises," "comprising," "includes," "including," "has," "having," or any variation thereof, are intended to cover a non-exclusive inclusion. For example, a process, method, article, or apparatus that comprises a list of features is not necessarily limited only to those features but may include other features not expressly listed or inherent to such process, method, article, or apparatus.

References to "one embodiment," "an embodiment," or "in embodiments" mean that the feature being referred to is included in at least one embodiment of the invention. Moreover, separate references to "one embodiment," "an embodiment," or "embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or not present), and both A and B are true (or present).

As used herein, "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawings, and which are shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

DETAILED DESCRIPTION OF THE DRAWING

Figure 1:
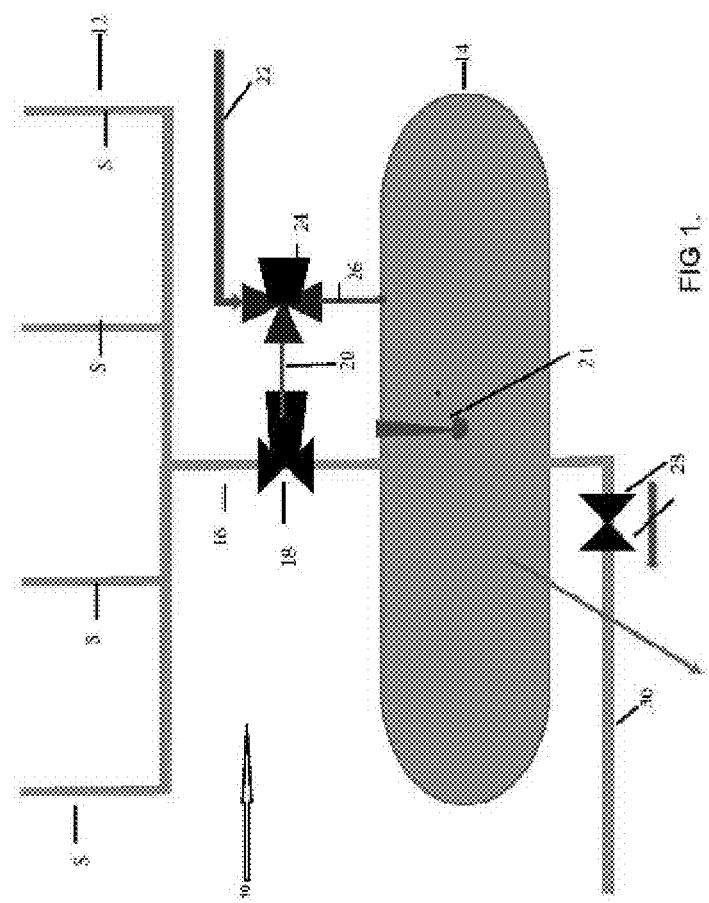
FIG. 1 is a schematic view of a first embodiment of the invention.

FIG. 1 is a schematic suggestive of a larger system 10 with a common reservoir for collecting from a series of vent header inputs S of manifold 12. The header inputs S are constructed to ensure that the lowest points connect the dropout source drains S to a common collection conduit 16 which drains, by gravity, to a common collecting tank/reservoir 14. Notably, when used to collect flammable/explosive liquids, such as those commonly produced during NGL processing, the tank/reservoir must be electrically grounded to earth ground to avoid the risk of unintended ignition resulting from a spark and to comply with prevailing certification. The conduit 16 incorporates a valve 18 which in the illustrated embodiment is a normally-open, directional ball valve pneumatically actuated by pressurized gas from a source 22. To enhance safety, preferably the gas source possesses flame retardancy. Nitrogen is one such well-known and economically available gas. The gas is communicated from a storage tank through input line 20. One example of a valve assembly is an actuator/ball valve assembly combining an Actuator Model MS 151-DA coupled with a Model SS-43GXS4 3-way valve available from Swagelok of Solon, Ohio.

In the embodiment of FIG. 1, the electrically energizable solenoid valve 24 connects the pressure source 22 to the input line 20. One example of such a solenoid valve 24 is an Asco Solenoid Model EF8320G225 from ASCO of Florshem Park, N.J. which is generally in the open position until energized to switch to the closed position.

The ball valve 18 is in the normally open position permitting flow of liquid into the tank 14 but upon pneumatic actuation occasioned by the actuation of solenoid valve 24 to close, itself is switched to the closed position to prevent further liquid draining into the collecting tank 14 concomitantly with the closing of the drain, to provide introduction to the system of pressurized gas from the source 22 (preferably $N_2$) directed to the tank reservoir 14.

The ball valve actuation results from detection of a liquid level in the tank 14 exceeding a set maximum by a level sensor 21 in the tank 14. The level sensor may be mechanically, electrically, or wirelessly connected to the actuating solenoid 24. The predetermined maximum liquid level is preferably set to both prevent tank overfill with liquids and to prevent generation of gas pressure from tank evaporation sufficient to interfere with liquid dropout drainage to the tank from the manifold 12. The level sensor 21 can be of any appropriate style but preferable is a leakproof and explosion-proof float switch such as a Flotect L6 or Flotect L4 magnetically actuated electro-mechanical switch available from Flowtech Corp of Kalamazoo, Mich.

The embodiment of FIG. 1 includes a pressurized gas line 26 from the solenoid 20 feeding directly into the top of the tank 14 and liquid drain line 30 including an in-line check valve 28 at the bottom of the tank which possesses a rating adequate to prevent back flow into the tank 14 while allowing unrestricted liquid outflow from the tank 14 upon introduction of pressurized gas through the input line 26. A one-way poppet check valve with a 1/3 psig rating such as a Swagelok Model SS-4C-1/3 is appropriate for use as the valve 28.

The embodiment of the invention illustrated in FIG. 1, contemplates operation as follows. In standard operation, the solenoid 24 remains closed to allow for free drainage from the dropout collection manifold into the tank/reservoir 14. However, when the liquid level in the tank reservoir 14 reaches a pre-set maximum, the level sensor activates and generates an actuation signal. Upon receiving the actuation signal from level sensor 21, the solenoid 24 is activated to direct pressurized gas into the line 20 to prevent additional inflow to the tank by closing the valve 18 and to open input line 26 to direct pressurized gas into the tank 14. The pressurized gas, with gravity assist, purges the liquid content in the tank 14 through the drain line 30. The purged liquid is then directed to a select destination either for recycling reclamation or further processing.

Figure 2:
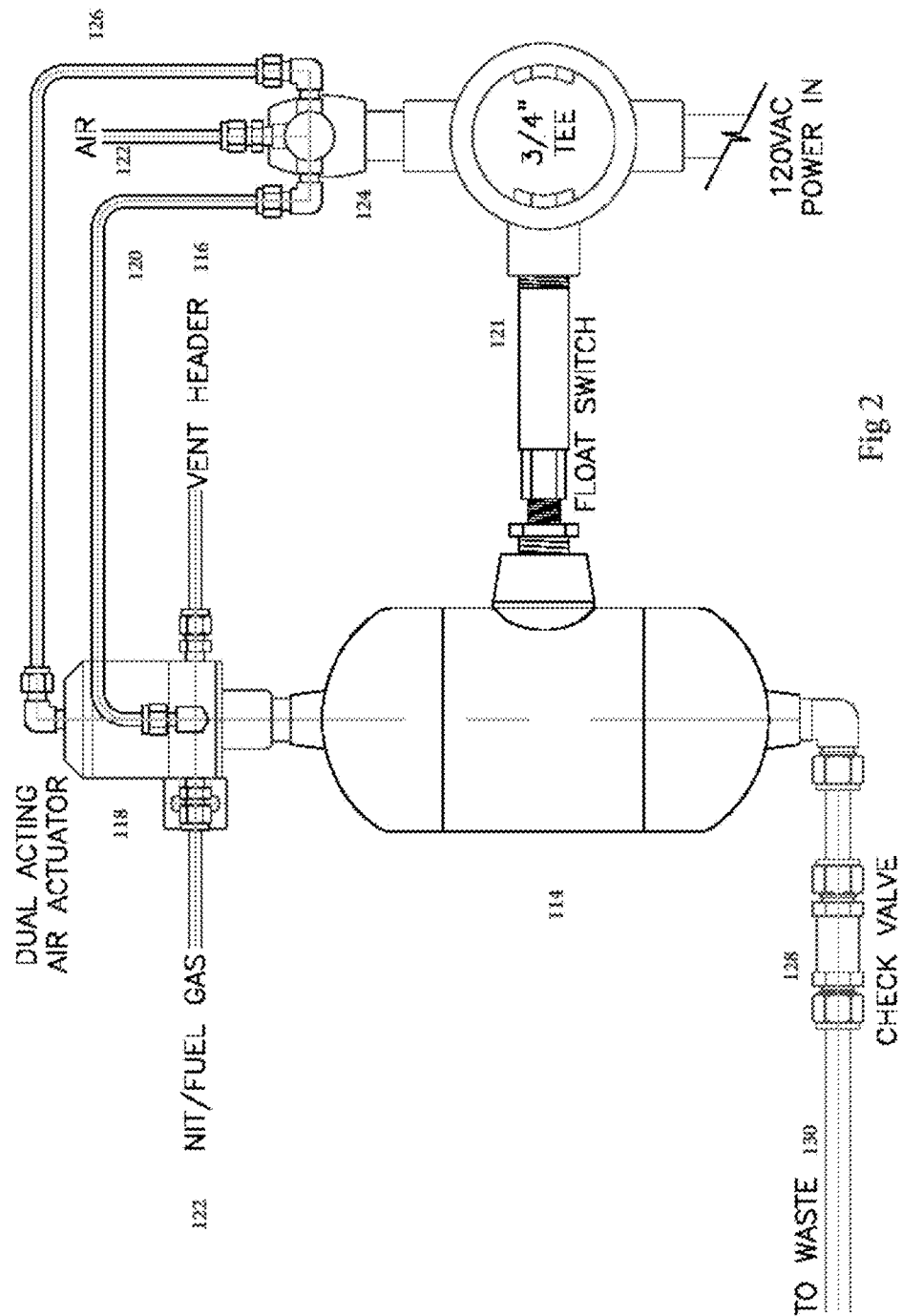
FIG. 2 is a component drawing of another embodiment of the invention.

The embodiment of FIG. 2 represents a smaller collection reservoir system than that represented by the schematic of FIG. 1. The generally vertically-oriented collecting vessel 114 includes an upper input associated with a pneumatically actuated dual acting switch 118 and a lower drain line 130 incorporating a check valve 128. A magnetic float switch 121 is mounted directly to the collecting vessel 114 and projects from its side. The float switch 121 is connected to a programmable logic controller (PLC) or even a proportional-integral-derivative (PID) controller (such as a Watlow controller) that is electrically connected to a solenoid flow controller 124. The solenoid 124 controls the output flow from pressurized instrument air line 122, ball valve actuator 118, activation line 126, and pressurized air vessel purge line 120.

In normal, draining operation, vent header line 116 is connected to a sample analyzer outlet line and is open to discharge liquid by gravity into the vessel 114. When float switch senses a liquid level in the vessel 114 that exceeds the preset minimum, a signal is directed to the controller which, in turn, generates an actuation signal to the solenoid 124. The solenoid switches to introduce pressurized air to the ball valve actuator 118 to close vent header 116 and open line 120 to purge the liquid content of the vessel 114 through the lower drain line 130. Following activation and purging, the float switch resumes its normal positon, terminates the signal to the controller which in turn terminates the activation of the solenoid 124. Once solenoid 124 is deactivated, purge air line 120 is closed, pressurization of line 126 is terminated, releasing the ball valve 118 to assume the open position and resume fluid drainage from the vent header line 116.

Although only two embodiments of the invention have been illustrated in the forgoing specification, it should be understood by those skilled in the art that many modifications and embodiments of the invention will come to mind to which the invention pertains, having benefit of the teaching presented in the foregoing description and associated drawing. For example, the tubing and fittings preferably should be composed from stainless steel. The selection of particular valving used should depend on particular factors associated with the intended use and, for example, as an automated system as in the described embodiments. Selection of mode of actuation will depend on factors such as the level of manual labor designated for the system and accessibility of the switch. Selection of the pressurized gas media used to drive the evacuation of the chamber will depend on factors such as the nature of the liquid waste and/or the requirements for greater or lesser downstream pressure applied to the waste resident in the collection vessel.

It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

I claim:

1. A system for liquid waste reservoir level control, comprising:
   a vent header in fluid communication with a source of liquid dropout condensate;
   a containment reservoir, including a containment reservoir input and a containment reservoir output, said containment reservoir output being in fluid communication with a liquid drain line;
   a multi-directional valve incorporating at least a first and second communicating orifices, said vent header being in fluid communication with and connected to said first communicating orifice;
   said second valve orifice being in fluid communication with said containment reservoir input;
   a pneumatic pressure source containing pressurized media, said pressure source being in pressurizing communication with said containment reservoir;
   at least one pressurized media input line disposed between said multi-directional valve and said pneumatic pressure source, said pressurized media input line being able to carry pressurized media from said source to said valve;
   an actuatable switch in fluid communication with and disposed between said pressure source and said containment reservoir, and
   a sensor disposed in the containment reservoir and in communication with the actuatable switch, said sensor being able to detect a specified containment reservoir liquid level.

2. The system of claim 1, wherein the containment reservoir is disposed underlyingly proximate said vent header, where said vent header is in fluid communication with an output from an analyzer.

3. The system of claim 1, wherein the multi-directional valve is a ball valve.

4. The system of claim 1, wherein the sensor is a float switch.

5. The system of claim 1, wherein the external pressurized media is nitrogen gas.

6. The system of claim 1, wherein the reservoir is electrically grounded to earth ground.

7. The system of claim 1, wherein a check valve is disposed along the liquid drain line connected to the reservoir output.

8. The system of claim 1, wherein the vent header is downstream of a sample analyzer gas source.

9. A method of controlling liquid level in a containment reservoir system including a liquid input and a liquid output, a multi-directional valve in fluid communication with the liquid input the multidirectional valve being movable between a first open position and a second closed position, a solenoid valve actuatable upon receiving an actuating signal, a source of pneumatic pressure, a pneumatic pressure communication conduit extending between the solenoid valve and the multidirectional valve, and a liquid level sensor for generating an actuating signal upon detection of a liquid level in the liquid containment reservoir exceeding a preselected maximum, the method comprising the steps of:
   a. sensing the liquid level in the liquid containment reservoir;
   b. generating an actuating signal upon detection of a liquid level exceeding a preselected maximum;
   c. communicating the actuating signal to the solenoid valve;
   d. energizing the solenoid valve to communicate pneumatic pressure to the multidirectional valve through the communication conduit;
   e. moving the multi-directional valve from the first open position to the second closed position and preventing further accumulation of liquid in the liquid containment reservoir; and
   f. introducing pneumatic pressure into the liquid containment reservoir to purge the contained liquid through the liquid output.

* * * * *